(12) United States Patent
Chiou et al.

(10) Patent No.: US 6,974,529 B2
(45) Date of Patent: Dec. 13, 2005

(54) HAND-HELD ELECTROPHORESIS DETECTION DEVICE AND SUPPORT THEREOF

(75) Inventors: Chung-Fan Chiou, Hsinchu (TW); Chih-Wei Ho, Miaoli (TW); Bor-Iuan Jan, Pingtung (TW); Jian Je Jian, Hsinchu (TW); Chien-Tsung Wu, Taichung (TW); Hsi-Hsin Shih, Taichung (TW)

(73) Assignee: Industrial Technology Research Institute, (TW)

( * ) Notice: Subject to any disclaimer, the term of this patent is extended or adjusted under 35 U.S.C. 154(b) by 443 days.

(21) Appl. No.: 10/316,017

(22) Filed: Dec. 11, 2002

(65) Prior Publication Data

US 2004/0031687 A1 Feb. 19, 2004

(30) Foreign Application Priority Data

Aug. 14, 2002 (TW) .............................. 91118285 A (51) Int. Cl.[7] ...................... G01N 27/453; B01D 85/00

(52) U.S. Cl. ...................................... 204/601; 206/722
(58) Field of Search ............................... 204/601–606, 204/616, 450, 451–456, 466, 461, 462; 206/724, 206/722

(56) References Cited

FOREIGN PATENT DOCUMENTS

| JP | 07-215137 A | * | 8/1995 | ........... B60R 11/02 |
| WO | WO 92/04958 A1 | * | 4/1992 | .......... B01D 15/08 |

OTHER PUBLICATIONS

JPO computer translaito of 07-215137 (Tatsuta Takeshi).*

* cited by examiner

Primary Examiner—Alex Noguerola
(74) Attorney, Agent, or Firm—Sughrue Mion, PLLC (57) ABSTRACT

A hand-held electrophoresis detection device and support thereof. The hand-held electrophoresis detection device includes a support and a cartridge. The cartridge attaches a sample, and is disposed in the support in a detachable manner.

8 Claims, 10 Drawing Sheets

HAND-HELD ELECTROPHORESIS DETECTION DEVICE AND SUPPORT THEREOF

BACKGROUND OF THE INVENTION

1. Field of the Invention

The invention relates to a hand-held electrophoresis detection device and support thereof; in particular, to a hand-held electrophoresis detection device with a support that can properly hold a cartridge therein.

2. Description of the Related Art

Figure 1:
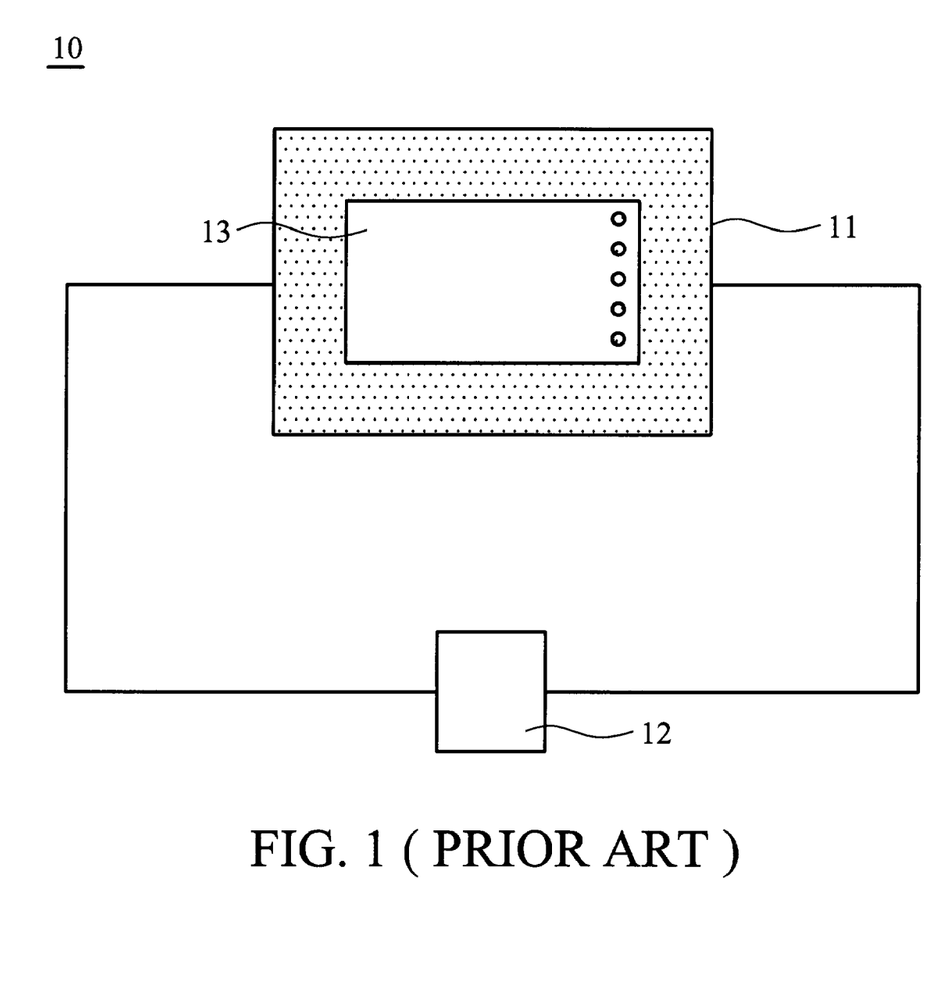
FIG. 1 is a schematic view of a conventional gel electrophoresis apparatus.

The value of electrophoresis in biochemistry has been recognized for some time in the analysis, for example, of proteins in serum as well as other body fluids. FIG. 1 shows a conventional gel electrophoresis apparatus 10. The apparatus 10 comprises a separation tank 11, and a power supply 12 electrically coupled to the separation tank 11. During analysis, a sample is applied near one edge of a layer of gelatin carried on a flexible sheet, usually called a "gel" 13. The gel 13 is disposed in the separation tank 11, and is electrophoresis by the power supply 12, stained and the density of the resulting pattern is measured to reveal the proteins contained in the sample.

Although gel electrophoresis is relatively inexpensive in terms of the supplies and equipment required to perform sample analyses, the technique requires skilled technicians and is time consuming, effectively resulting in a high price per test and limiting the number of tests that can be performed using the technique.

Efforts have been made to automate electrophoresis in clinical laboratories. For example, capillary electrophoresis is a more recent development and can be used to perform the type of electrophoresis separations presently performed with gels.

Figure 2:
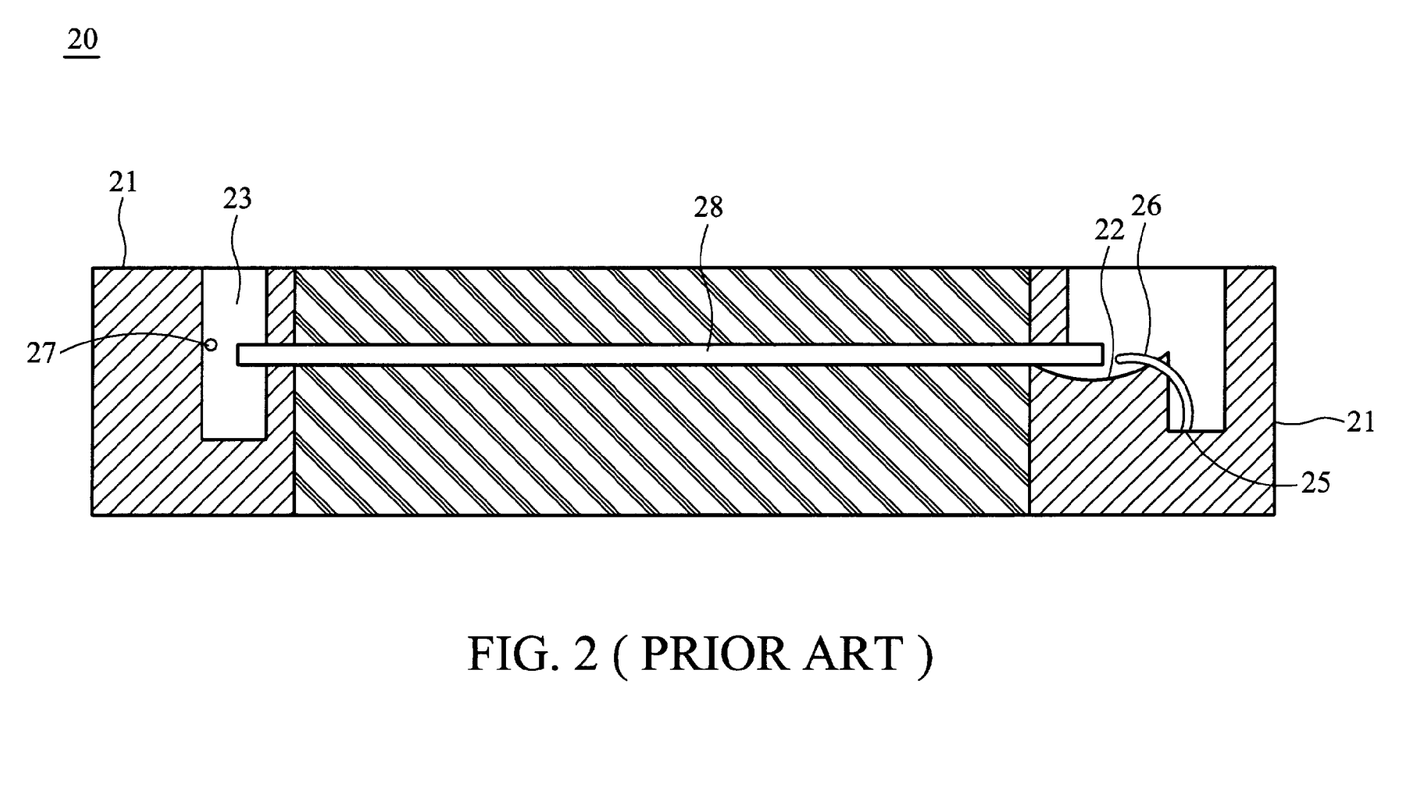
FIG. 2 is a schematic view of a conventional capillary electrophoresis analyzer as described in U.S. Pat. No. 5,560,811.

Automated forms of capillary electrophoresis analyzers are known in the art. For example, FIG. 2 shows a conventional capillary electrophoresis analyzer 20 described in U.S. Pat. No. 5,560,811. An electrophoresis separation plate 21 has a plurality of sample wells 22 at one end and a common buffer reservoir 23 at the other end. A first master electrode 25 is electrically connected to a cell electrode 26 in the sample wells 22. A second master electrode 27 is in the common buffer reservoir 23. Capillary electrophoresis columns 28 are mounted in the plate 21 so that there is electrical communication between the first master electrode 25 by way of the capillary electrophoresis column 28 when the sample wells 22 and the reservoir 23 are filled with electrically conductive liquid. In operation, current between the master electrodes permits electrophoresis of the sample from the sample well 22 to the reservoir 23.

Other automated capillary electrophoresis apparatuses are described in U.S. Pat. No. 6,132,582, U.S. Pat. No. 5,885,430, U.S. Pat. No. 6,118,127, U.S. Pat. No. 5,413,686.

None of the automated analyzers described, however, are suitable for routine clinical laboratory applications. Each requires considerable manual manipulation despite their automated nature, such as preparation and placement of individual sample and buffer vials onto the analyzer, programming for the various analytical routines, and the like. Because only one sample can undergo electrophoresis and detection during each analysis cycle of the analyzers, the number of samples per unit time, or throughput, is severely restricted compared to the needs of most routine clinical laboratory work.

Figure 3:
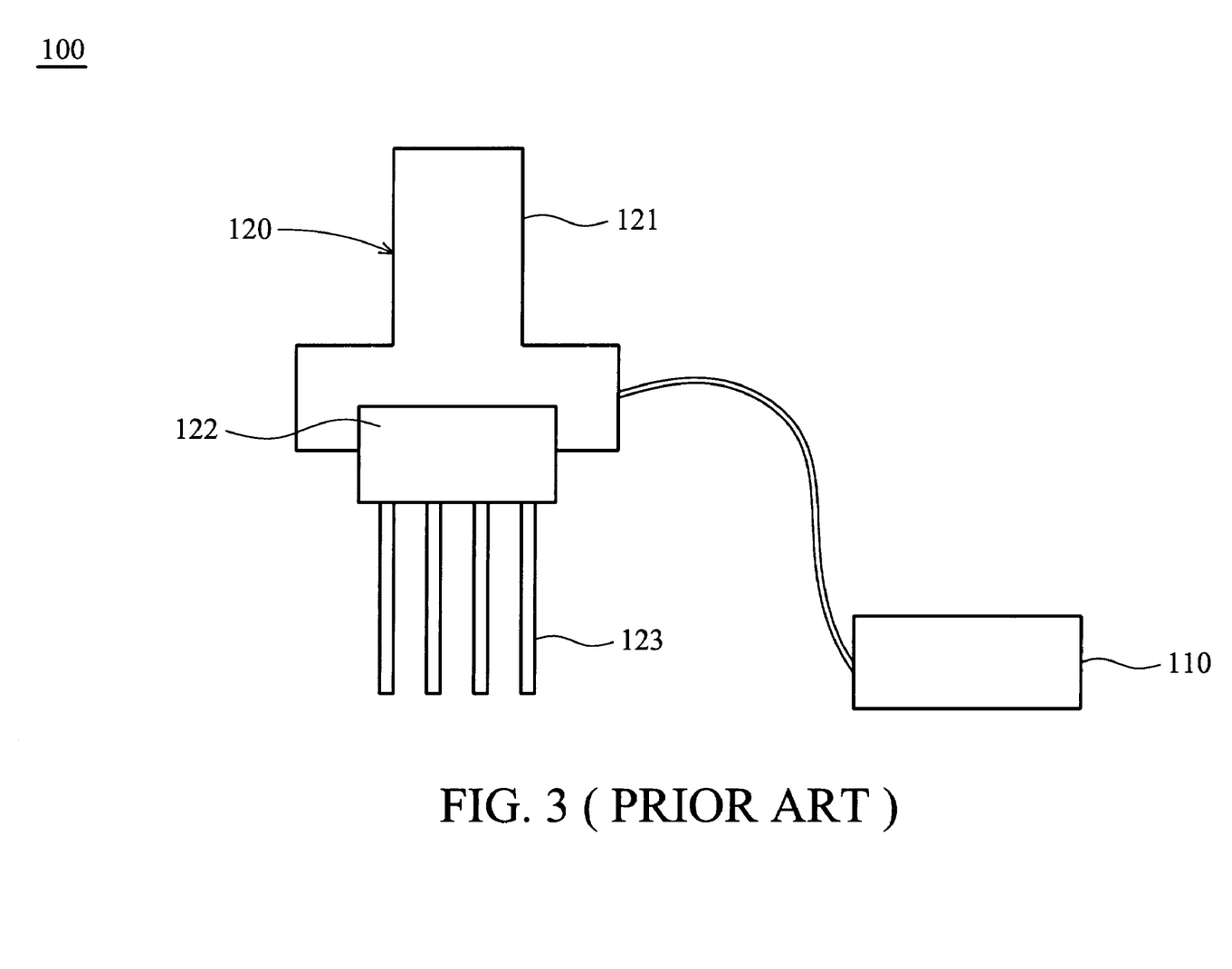
FIG. 3 is a schematic view of a conventional electrophoresis separation apparatus.

In view of the disadvantages of the conventional analyzers, the inventor of this invention has provided a new electrophoresis separation apparatus 100 as shown in FIG. 3. The apparatus 100 includes a main portion 110 and a hand-held electrophoresis detection device 120. Since the hand-held electrophoresis detection device 120 is connected to the main portion 110 in a separable manner, it can be operated conveniently without the limitation of the location of the main portion 110. Thus, the detection can be performed more quickly and conveniently.

The main portion 110 controls a detection of the sample. The hand-held electrophoresis detection device 120 includes a support 121, a cartridge 122, and a plurality of detection columns 123. The support 121 is used as a basic element of the device 120, and is electrically connected to the main portion 110. The cartridge 122 is disposed in the support 121 in a detachable manner, and is electrically connected to the support 122. After the detection is finished, the cartridge 122 can be replaced quickly so that the intermixing between the samples can be avoided. The detection columns 123 are disposed on the cartridge 122, and are used for the samples to be attached thereto. Thus, the samples can be moved in the detection columns 123 to perform the detection.

In the electrophoresis separation apparatus 100, only the basic structure of the apparatus is described. However, the detailed structure of each element is not described, such as the structure inside the support, and the assembly/disassembly manner between the cartridge and the support.

SUMMARY OF THE INVENTION

In view of this, the invention provides a hand-held electrophoresis detection device with a support that can properly hold a cartridge therein.

Accordingly, the invention provides a hand-held electrophoresis detection device. The hand-held electrophoresis detection device includes a support and a cartridge. The support comprises a housing, a first moving member, a second moving member, and a rotating member. The first moving member is disposed in the housing in a moveable manner. The second moving member is disposed in the housing in a moveable manner, and abuts the first moving member. The rotating member is disposed in the housing in a rotatable manner, and abuts the second moving member. The cartridge attaches a sample, and is disposed in the support in a detachable manner. When the cartridge is inserted into the housing of the support, the first moving member is abutted and moved by the cartridge. Then, the second moving member is moved by the first moving member to rotate the rotating member so that the cartridge is held in the support by the rotating member.

In a preferred embodiment, the first moving member is moved in a first direction in which the cartridge is inserted into the support, and the second moving member is moved in a second direction normal to the first direction.

In another preferred embodiment, the support further comprises a pivot. The pivot is disposed in the housing, and holds the rotating member. The rotating member is rotated relative to the pivot.

In another preferred embodiment, the number of the second moving member is two, and the first moving member includes two abutting portions to abut the second moving member respectively, and a gap is formed between the abutting portions.

Furthermore, the first moving member includes a base portion abutting the cartridge, and the abutting portions are integrally formed on the base portion.

Furthermore, each of the abutting portions is formed at a predetermined angle inclined from to the first direction. The base portion is substantially U-shaped. Each of the second moving members includes a curved surface abutting the first moving member.

In another preferred embodiment, the rotating member includes a hook for holding the cartridge.

In another preferred embodiment, the rotating member includes a push portion.

Furthermore, the housing includes a tapered portion near the first groove.

In another preferred embodiment, the housing includes a first groove, and the cartridge includes a rail corresponding to the first groove, whereby the cartridge is guided into the support by the rail inserting into the first groove.

In another preferred embodiment, the support includes a first contact, and the cartridge includes a second contact corresponding to the first contact, whereby the cartridge is electrically connected to the support by the first contact and the second contact.

In another preferred embodiment, the housing includes a second groove, and the cartridge includes a protrusion corresponding to the second groove, whereby the cartridge is guided into the support by the protrusion inserting into the second groove.

In another preferred embodiment, the cartridge includes a step portion for the rotating member to hold.

The invention also provides a support for holding a cartridge of a hand-held electrophoresis detection device. The support comprises a housing, a first moving member, a second moving member, and a rotating member. The first moving member is disposed in the housing in a moveable manner. The second moving member, abutting the first moving member, is disposed in the housing in a moveable manner. The rotating member, abutting the second moving member, is disposed in the housing in a rotatable manner. When the cartridge is inserted into the housing, the first moving member is abutted and moved by the cartridge, and the second moving member is moved by the first moving member to rotate the rotating member so that the cartridge is held in the housing by the rotating member.

The invention provides another hand-held electrophoresis detection device. The device is used for detecting samples, and comprises a support and a cartridge. The support includes a housing, an elastic member, and an abutting member. The elastic member is disposed in the housing, and the abutting member, abutting the elastic member, is disposed in the housing in a moveable manner. The cartridge, for attaching the samples, includes a concave portion, and is disposed in the support in a detachable manner. When the cartridge is inserted into the housing of the support, the abutting member of the support is located in the concave portion of the cartridge, and the cartridge is held in the support by the elastic member.

In another preferred embodiment, the elastic member is a spring.

In another preferred embodiment, the abutting member is a ball.

The invention provides another support for holding a cartridge of a hand-held electrophoresis detection device. The support comprises a housing, an elastic member, and an abutting member. The elastic member is disposed in the housing in a moveable manner. The abutting member, abutting the elastic member, is disposed in the housing in a rotatable manner. When the cartridge is inserted into the housing of the support, the abutting member of the support is located in the concave portion of the cartridge, and the cartridge is held in the support by the elastic member.

BRIEF DESCRIPTION OF THE DRAWINGS

The invention is hereinafter described in detail with reference to the accompanying drawings in which:

FIG. 4b is a schematic view of a support in FIG. 4a;

FIG. 5a~5c are schematic views of assembly steps between a cartridge and the support in FIG. 4a;

FIG. 6a, and FIG. 6b are schematic views of separation steps between the cartridge and the support in FIG. 4a.

DETAILED DESCRIPTION OF THE INVENTION

First Embodiment

Figure 4A:
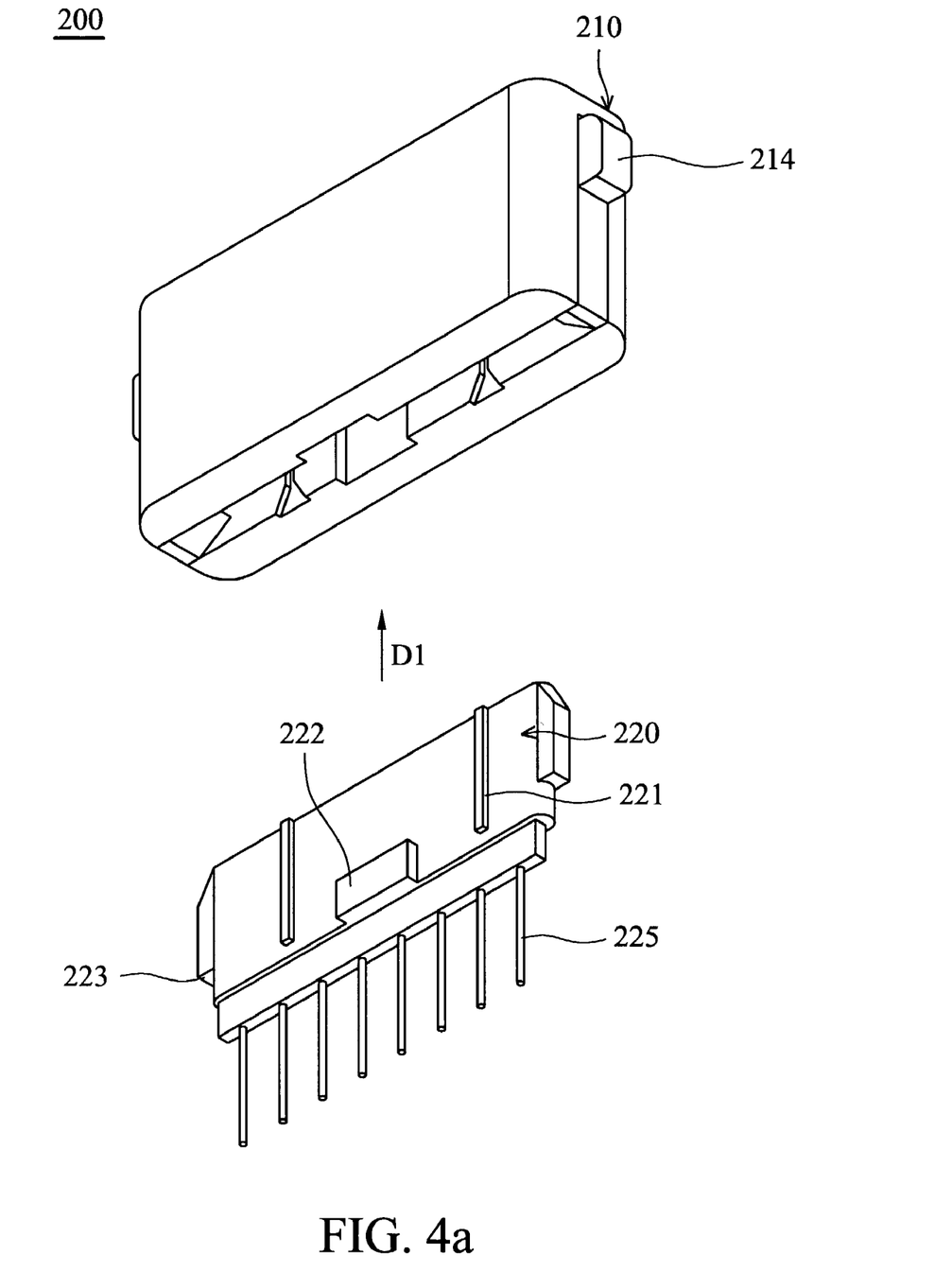
FIG. 4a is a schematic view of a hand-held electrophoresis detection device as disclosed in a first embodiment of this invention.
Figure 4B:
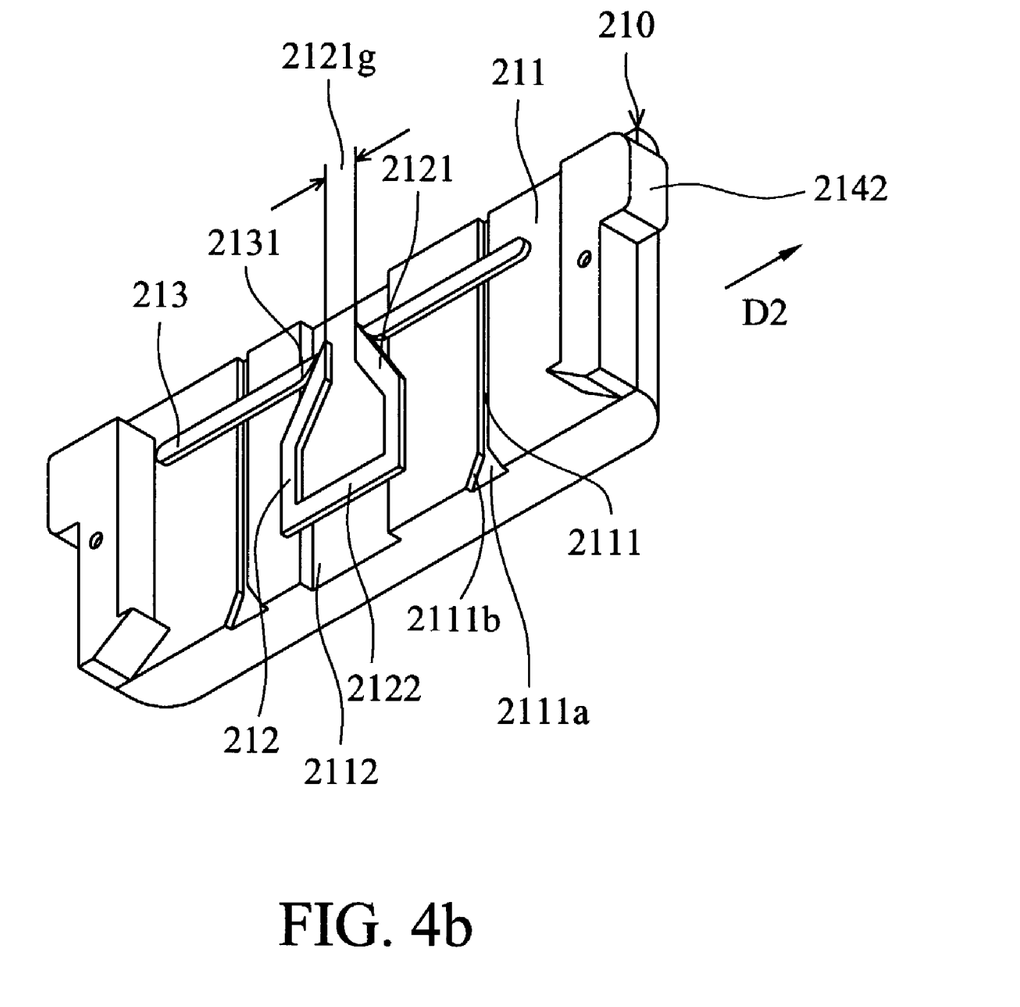

Referring to FIG. 4a and FIG. 4b, a hand-held electrophoresis detection device 200, as disclosed in a first embodiment of this invention, is used to detect samples, and includes a support 210 and a cartridge 220. The support 210 comprises a housing 211, a first moving member 212, two second moving member 213, two rotating members 214, and two pivots 215.

The housing 211 is used as a basic element of the support 210, and includes two first grooves 2111, and a second groove 2112. The second groove 2112 is formed at the center portion of the housing 211, and each of the first grooves 2111 is formed beside the second groove 2112. The housing 211 includes two inlets 2111a in the first grooves 2111 respectively. A tapered portion 2111b is formed near the inlet 2111a of the first groove 2111 so that the cartridge 220 can be smoothly inserted into the housing 211 of the support 210.

The first moving member 212 is disposed in the housing 211 in a moveable manner, and is moved in a first direction D1 in which the cartridge 220 is inserted into the support 210. Furthermore, the first moving member 212 is divided into a base portion 2122 and two abutting portions 2121. The base portion 2122 is substantially U-shaped, and is abutted by the cartridge 220 inserted into the support 210. Each of the abutting portions 2121 is integrally formed on the base portion 2122, and is formed at a predetermined angle inclined from the first direction D1. Each of the abutting portions 2121 is abutted by the second moving member 213 respectively, and a gap 2121g is formed between the abutting portions 2121.

Each of the second moving members 213 is disposed in the housing 210 in a moveable manner, and is abutted by the abutting portion 2121 of the first moving member 212 respectively. Each of the second moving members 213 is moved in a second direction D2 normal to the first direction D1. Furthermore, each of the second moving members 213 includes a curved surface 2131 abutting the first moving member 212. Thus, the adjacent surfaces between the first moving member 212 and the second moving members 213 are not parallel. As a result, the force of the upward movement of the first moving member 212 can be smoothly transferred into the lateral movement of the second moving members 213.

Each of the rotating members 214 is disposed in the housing 211 in a rotatable manner, and is abutted by the second moving member 213 respectively. Furthermore, each of the rotating members 214 includes a hook 2141 and a push portion 2142. When the cartridge 220 is inserted into the support 210, it is held by the hooks 2141 of the rotating members 214. It is noted that the user can rotate the rotating members 214 via the push portions 2142.

Each of the pivots 215 is disposed in the housing 211, and holds the rotating members 214 in the housing 211. That is, each of the rotating members 214 is rotated relative to the pivot 215 respectively.

Figure 5A:
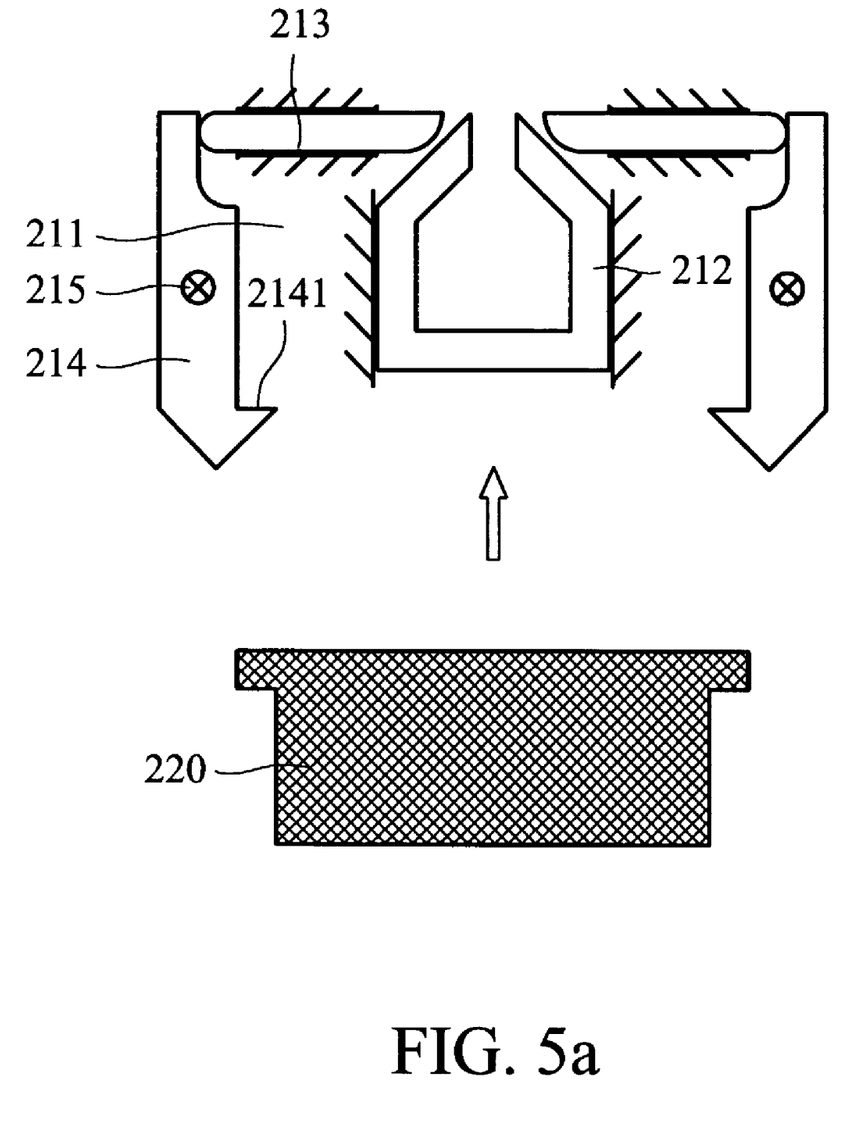
Figure 5B:
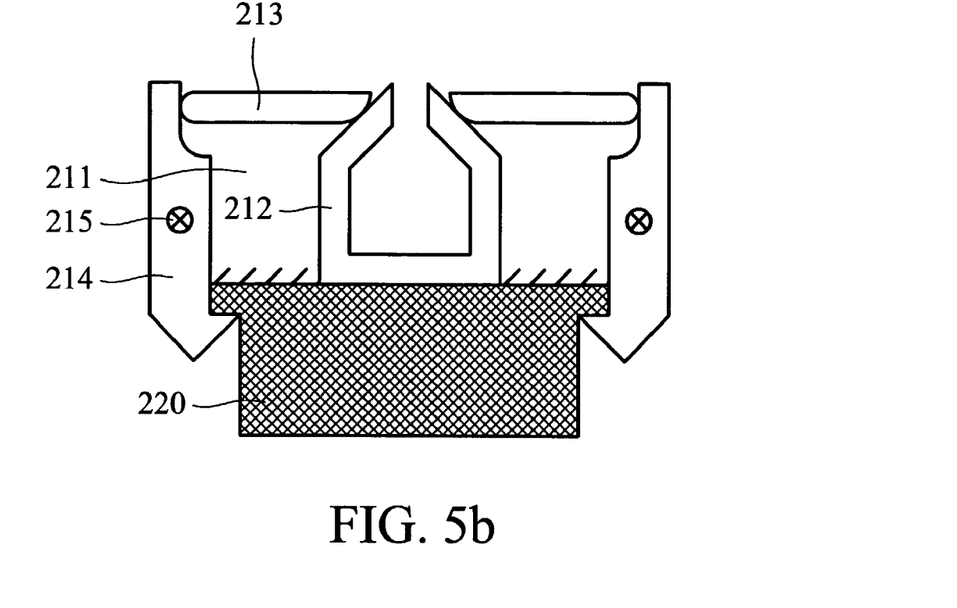
Figure 5C:
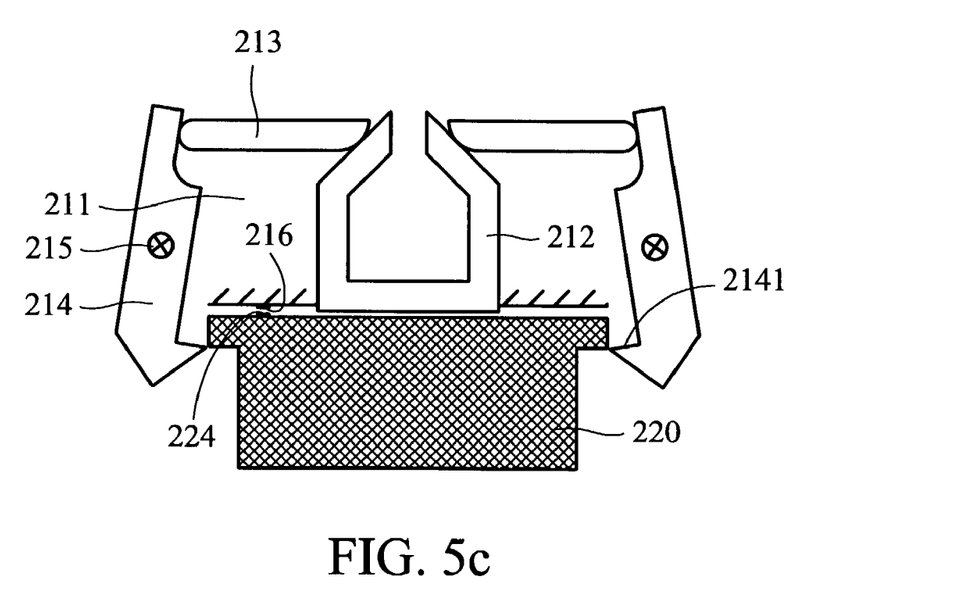

In addition, the support 210 includes a first contact 216 as shown in FIG. 5c. The first contact 216 is used as an intermediate device for electrically coupling the cartridge 220 and the support 210.

The cartridge 220 is disposed in the support 210 in a detachable manner, and includes two rails 221, a protrusion 222, two step portions 223, a second contact 224, and a plurality of detection columns 225. The sample is attached on the detecting column 225.

Each of the rails 221 corresponds to the first groove 2111 of the support 210 respectively. The protrusions 222 corresponds to the second groove 2112 of the support 210. The cartridge 220 can be guided into the support 210 by the rails 221 inserting into the first grooves 2111 and the protrusion 222 inserting into the second groove 2112. Furthermore, the step portions 223 can be engaged by the hooks 2141 of the rotating members 214 in the support 210.

The second contact 224 corresponds to the first contact 216 in the support 210 as shown in FIG. 5c. Thus, when the cartridge 220 is disposed in the support 210, the cartridge 220 is electrically connected to the support 210 by the second contact 224 contacting the first contact 216.

FIG. 5a, FIG. 5b, FIG. 5c, FIG. 6a, and FIG. 6b are schematic views of assembly/disassembly steps between the cartridge 220 and the support 210. It is noted that for the convenience of the descriptions, the shape of the step portions 223 is slightly different from that shown in FIG. 4a. Thus, it is understood that the shape or the position of the step portions 223 can be adjusted based on conditions.

To insert the cartridge 220 into the support 210, the cartridge 220 is positioned as shown in FIG. 5a. Then, the cartridge 220 is moved upwardly to abut the first moving member 212 and move the first moving member 212 upwardly. Subsequently, the second moving members 213 are moved laterally by the first moving member 212 via the curved surfaces 2131. Finally, the rotating members 214 are rotated by the second moving members 213 so that the step portions 223 of the cartridge 220 are engaged by the hooks 2141 of the rotating members 214. Thus, the cartridge 220 is held in the support 210 as shown in FIG. 5b.

It is noted that before the cartridge 220 is completely inserted into the support 210, the hooks 2141 of rotating members 214 may be stuck by both sides of the cartridge 220. However, when the cartridge 220 is continuously moved upwardly, the base portion 2122 of the first moving member 212 is slightly deformed inwardly as shown in FIG. 5c. Thus, the cartridge 220 can be kept moving upwardly, and the hooks 2141 of the rotating members 214 can keep rotating. As a result, after the hooks 2141 of the rotating members 214 are not stuck by the cartridge 220, the second moving members 213 can be kept moving laterally and the base portion 2122 of the first moving member 212 is not deformed anymore so that the cartridge 220 is held in the support 210.

Figure 6A:
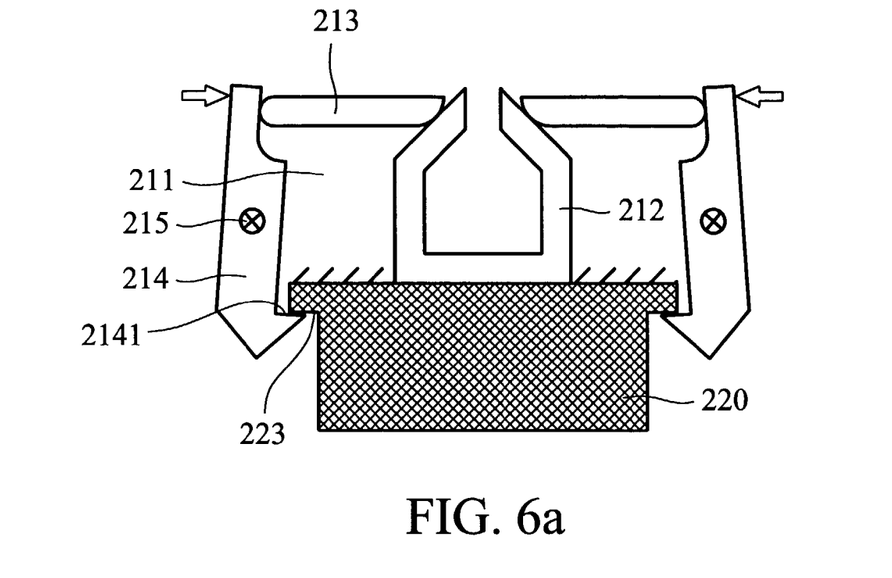
Figure 6B:
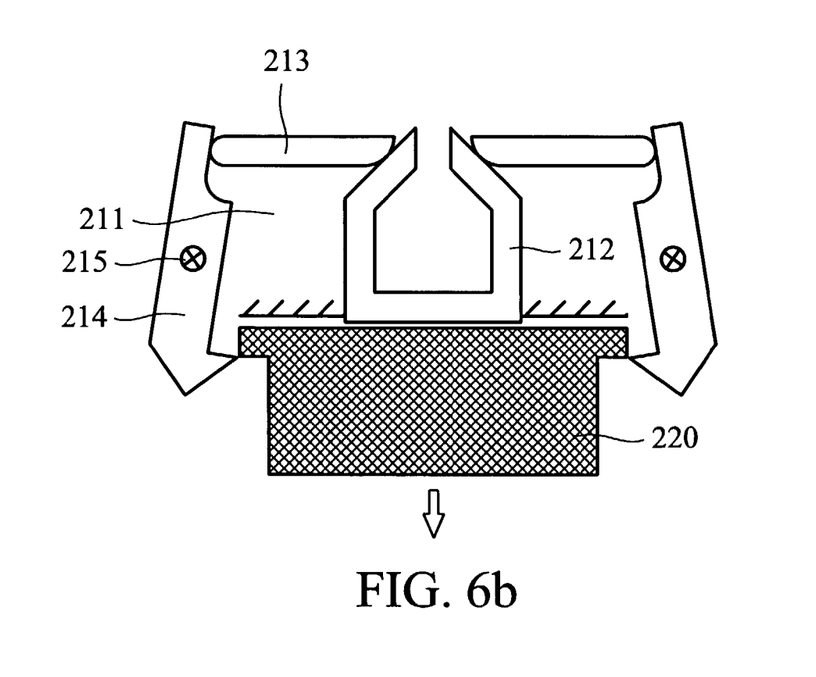

To remove the cartridge 220 from the support 210, the push portions 2142 of the rotating members 214 are pushed inwardly as shown in FIG. 6a so that the second moving members 213 are moved inwardly. At this time, since the hooks 2141 of the rotating members 214 are not completely disengaged from the step portions 223 of the cartridge 220, the first moving member 212 cannot be moved downwardly so that the base portion 2122 of the first moving member 212 is deformed inwardly. Until the hooks 2141 of the rotating members 214 are completely disengaged from the step portions 223 of the cartridge 220, the cartridge 220 is pushed downwardly due to the deformation energy of the first moving member 212 as shown in FIG. 6b.

As stated above, when the cartridge is inserted into the support, it can be held stably. Furthermore, since the structure inside the support is designed based on the concept of the linkages, the cartridge can be held by the hooks of the rotating members due to the force-transmission and the direction-transfer of the moving members. To remove the cartridge from the support, the push portions of the rotating members are pushed so that the moving members inside the support are moved in a direction opposite to the direction during the inserting to complete such operation.

Furthermore, in this operation, assembly/disassembly of the cartridge and the support is more convenient.

Second Embodiment

Figure 7A:
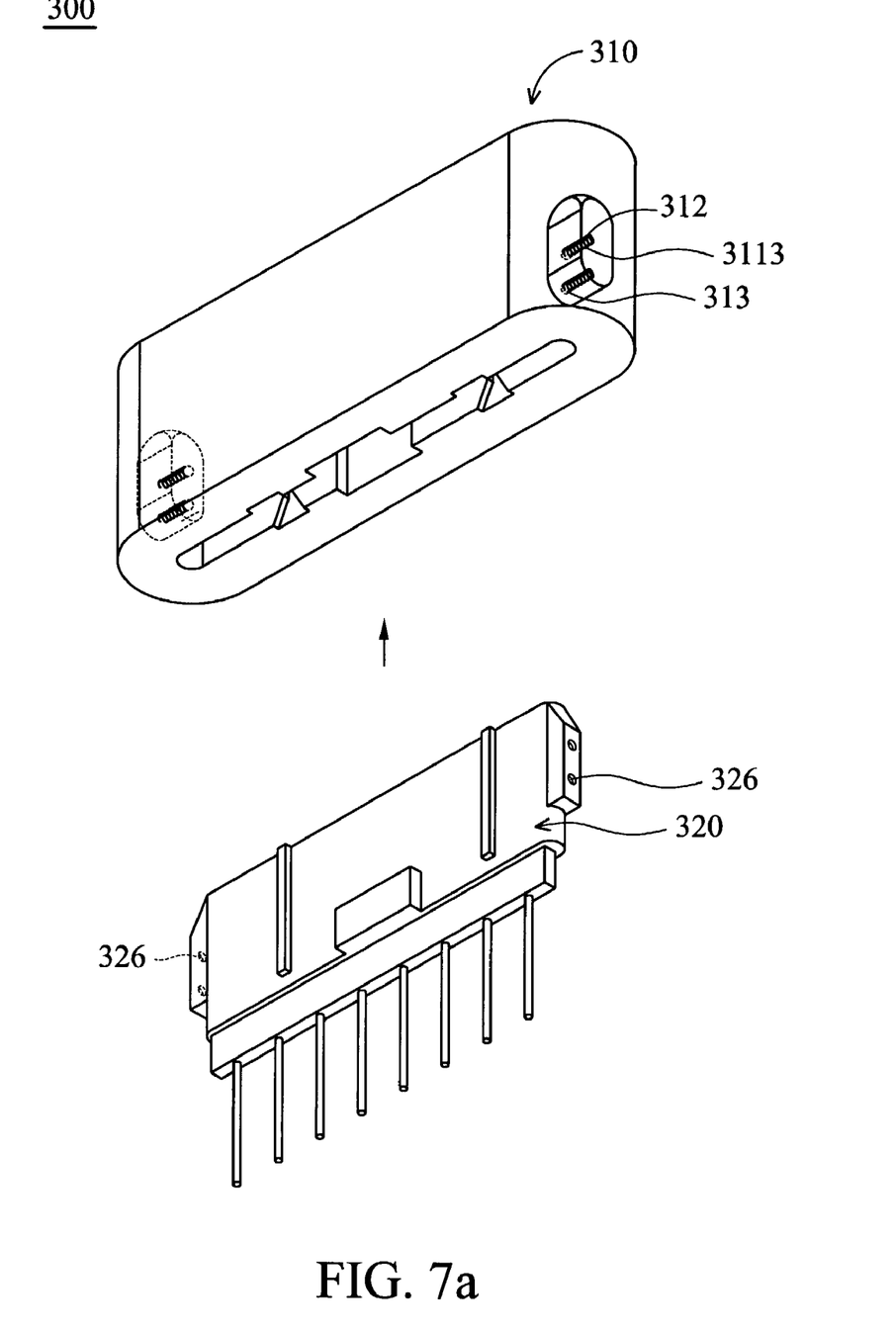
FIG. 7a and FIG. 7b are schematic views of a hand-held electrophoresis detection device as disclosed in a second embodiment of this invention.
Figure 7B:
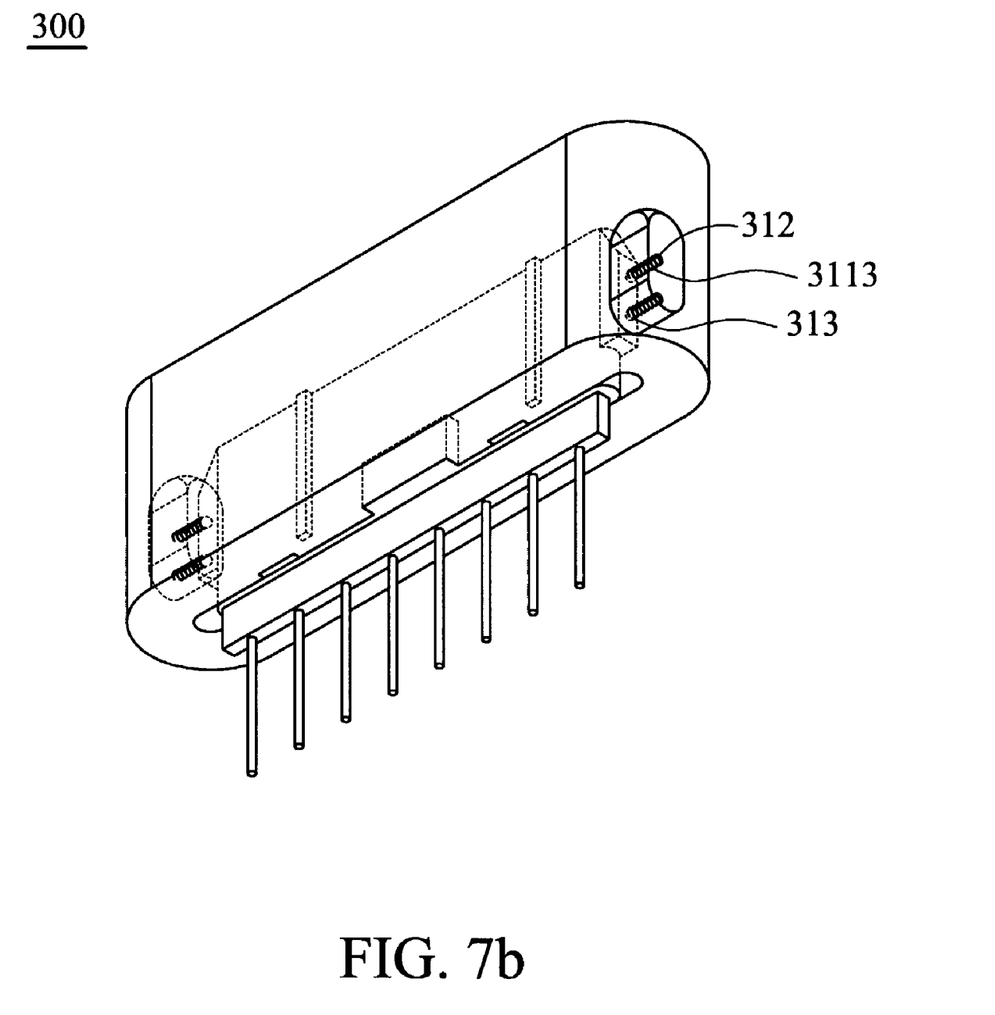

FIG. 7a and FIG. 7b are schematic views of a hand-held electrophoresis detection device 300 as disclosed in a second embodiment of this invention. In this embodiment, the description of the components same as those of the first embodiment is omitted.

The difference between the second embodiment and the first embodiment is that the first moving member 212, the second moving members 213 and the rotating member 214 of the first embodiment are replaced by four spring members 312 and four abutting members 313 in a support 310 of this embodiment. Also, four concave portions 326 are formed in a cartridge 320 of this embodiment. Each of the concave portions 326 corresponds to the abutting member 313 respectively. It is noted that in FIG. 7a, the number of the spring members 312 is four, and the number of the abutting members 313 is four, the number of the concave portions 326 is four. However, their number is not limited.

The elastic member 312 is disposed in a hole 3113 of a housing 311 of the support 310. The abutting member 313 abuts the elastic member 132, and is disposed in the hole 3113 of the housing 311 in a moveable manner. When the cartridge 320 is inserted into the housing 311 of the support 310 as shown in FIG. 7b, the abutting members 313 of the support 310 are located in the concave portions 326 of the cartridge 320, and the cartridge 320 is held in the support 310 by the elastic members 312.

It is understood that each of the elastic members 312 may be a spring, and each of the abutting members 313 may be a ball.

According to the structure of this embodiment, the cartridge can be stably held in the support, and assembly/disassembly of the cartridge and support is more convenient.

While the invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiments, those alternatives which have been discussed above, and all equivalents thereto.

What is claimed is:

1. A support for holding a cartridge of a hand-held electrophoresis detection device, comprising:
   a housing;
   a first moving member disposed in the housing in a moveable manner;
   a second moving member, abutting the first moving member, disposed in the housing in a moveable manner; and
   a rotating member, abutting the second moving member, disposed in the housing in a rotatable manner, wherein the first moving member is abutted and moved by the cartridge when the cartridge is inserted into the housing, and the second moving member is moved by the first moving member to rotate the rotating member so that the cartridge is held in the housing by the rotating member.

2. The support as claimed in claim 1, wherein the first moving member is moved in a first direction in which the cartridge is inserted into the support, and the second moving member is moved in a second direction normal to the first direction.

3. The support as claimed in claim 1, wherein the support further comprises a pivot, disposed in the housing, for holding the rotating member, wherein the rotating member is rotated relative to the pivot.

4. The support as claimed in claim 1, wherein the second moving member includes a curved surface abutting the first moving member.

5. The support as claimed in claim 1, wherein the rotating member includes a hook for holding the cartridge.

6. The support as claimed in claim 1, wherein the rotating member includes a push portion.

7. The support as claimed in claim 1, wherein the housing includes a first groove, a second groove, and a tapered portion near the first groove.

8. The support as claimed in claim 1, wherein the housing includes a first contact for electrically connecting with the cartridge.

* * * * *